(12) United States Patent
Norris (10) Patent No.: US 10,545,130 B2
(45) Date of Patent: Jan. 28, 2020

(54) TEXTURE ANALYSIS OF A COATED SURFACE USING ELECTROSTATICS CALCULATIONS

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 640 days.

(21) Appl. No.: 14/535,372

(22) Filed: Nov. 7, 2014

(65) Prior Publication Data

US 2015/0134299 A1 May 14, 2015

Related U.S. Application Data

(60) Provisional application No. 61/901,493, filed on Nov. 8, 2013.

(51) Int. Cl.
| | | |
|---|---|---|
| *G01N 33/32* | (2006.01) | |
| *G01N 21/25* | (2006.01) | |
| *G01N 21/55* | (2014.01) | |
| *G01J 3/50* | (2006.01) | |
| *G01J 3/46* | (2006.01) | |

(52) U.S. Cl.
CPC .............. *G01N 33/32* (2013.01); *G01J 3/462* (2013.01); *G01J 3/463* (2013.01); *G01J 3/504* (2013.01); *G01N 21/251* (2013.01); *G01N 21/55* (2013.01); *G01N 2201/12* (2013.01)

(58) Field of Classification Search
None
See application file for complete search history.

(56) References Cited

U.S. PATENT DOCUMENTS

| | | | |
|---|---|---|---|
| 3,379,553 A | * | 4/1968 | Dowley ................. G03G 13/06 399/294 |
| 3,927,944 A | | 12/1975 | Iwahashi |
| 3,972,617 A | | 8/1976 | Shibata |
| 4,092,069 A | | 5/1978 | Fukuda |
| 4,164,374 A | | 8/1979 | Lambe |
| 4,344,142 A | | 8/1982 | Diehr, II |
| 4,479,718 A | | 10/1984 | Alman |

(Continued)

FOREIGN PATENT DOCUMENTS

| | | |
|---|---|---|
| CN | 1495555 | 5/2004 |
| CN | 1635957 A | 7/2005 |

(Continued)

OTHER PUBLICATIONS

Li Sun and Richard M. Crooks in Molecular Interactions between Organized, Surface-Confined Monolayers and Vapor-Phase Probe Molecules. 5. Acid-Base Interactions, 1993 American Chemical Society, pp. 1775-1780.*

(Continued)

*Primary Examiner* — Tung S Lau
(74) *Attorney, Agent, or Firm* — W. Brad Barger (57) ABSTRACT

A method that includes obtaining, using a processor, reflectance data from a target coating and calculating, using the processor, electrostatics data from the reflectance data. The method also includes generating, using the processor, a coating formulation that is the same or substantially similar in appearance to the target coating.

11 Claims, 7 Drawing Sheets

(56) References Cited

U.S. PATENT DOCUMENTS

| | | | |
|---|---|---|---|
| 4,544,424 A * | 10/1985 | Take | E04C 2/043 |
| | | | 156/284 |
| 4,711,580 A | 12/1987 | Venable | |
| 5,231,472 A | 7/1993 | Marcus | |
| 5,319,437 A | 6/1994 | Van Aken | |
| 5,590,251 A | 12/1996 | Takagi | |
| 5,612,928 A | 3/1997 | Haley | |
| 5,926,262 A | 7/1999 | Jung | |
| 6,056,821 A * | 5/2000 | Nihongi | B05B 5/08 |
| | | | 118/621 |
| 6,166,841 A | 12/2000 | Pringle | |
| 6,249,751 B1 | 6/2001 | Asaba et al. | |
| 6,362,885 B1 * | 3/2002 | Osumi | G01J 3/46 |
| | | | 356/402 |
| 6,449,384 B2 | 9/2002 | Di Venuto | |
| 6,539,325 B1 * | 3/2003 | Numata | G01J 3/46 |
| | | | 356/402 |
| 6,794,669 B2 | 9/2004 | Chelvayohan et al. | |
| 7,809,155 B2 | 10/2010 | Nestares | |
| 7,944,561 B2 | 5/2011 | Nisper et al. | |
| 8,345,252 B2 | 1/2013 | Nisper et al. | |
| 8,606,731 B2 | 12/2013 | Fujieda et al. | |
| 8,879,066 B2 * | 11/2014 | Norris | G01N 21/25 |
| | | | 356/445 |
| 9,482,657 B2 * | 11/2016 | Bell | G01N 33/32 |
| 2002/0063960 A1 * | 5/2002 | Fritz | E01F 9/619 |
| | | | 359/515 |
| 2003/0208345 A1 | 11/2003 | O'Neill | |
| 2003/0223060 A1 | 12/2003 | Graf et al. | |
| 2005/0128484 A1 | 6/2005 | Rodrigues | |
| 2005/0169518 A1 | 8/2005 | Boston et al. | |
| 2005/0206383 A1 | 9/2005 | Park | |
| 2006/0030060 A1 | 2/2006 | Noguchi et al. | |
| 2006/0045831 A1 | 3/2006 | Galembeck | |
| 2006/0245632 A1 | 11/2006 | Nisper et al. | |
| 2007/0019887 A1 | 1/2007 | Nestares | |
| 2007/0172113 A1 | 7/2007 | Sai et al. | |
| 2007/0200337 A1 | 8/2007 | Johnson et al. | |
| 2007/0226158 A1 | 9/2007 | Woronow | |
| 2007/0250273 A1 | 10/2007 | De Haas | |
| 2008/0177586 A1 | 7/2008 | Jamjoom | |
| 2008/0235224 A1 * | 9/2008 | Rodrigues | B05D 5/005 |
| 2008/0278723 A1 | 11/2008 | Merchak | |
| 2009/0015835 A1 | 1/2009 | Balakrishnen et al. | |
| 2009/0157212 A1 | 6/2009 | McClanahan | |
| 2009/0190839 A1 | 7/2009 | Higgins | |
| 2009/0213120 A1 | 8/2009 | Nisper et al. | |
| 2009/0292520 A1 | 11/2009 | Nwankpa | |
| 2010/0048242 A1 | 2/2010 | Rhoads | |
| 2010/0228511 A1 | 9/2010 | Chin et al. | |
| 2011/0242562 A1 | 10/2011 | Vrhel | |
| 2011/0282613 A1 | 11/2011 | Skinner | |
| 2012/0225190 A1 | 9/2012 | Steenhoek | |
| 2012/0243797 A1 | 9/2012 | Di Venuto | |
| 2012/0303376 A1 | 11/2012 | Shishido | |
| 2013/0244197 A1 | 9/2013 | Tijoe | |
| 2014/0064786 A1 * | 3/2014 | Mogi | G03G 15/2053 |
| | | | 399/122 |
| 2014/0078293 A1 * | 3/2014 | Beymore | G01J 3/504 |
| | | | 348/135 |
| 2014/0118936 A1 | 5/2014 | Merlet et al. | |
| 2014/0242271 A1 | 8/2014 | Prakash et al. | |
| 2014/0250109 A1 | 9/2014 | Wang | |
| 2014/0278251 A1 * | 9/2014 | Norris | G06F 19/703 |
| | | | 702/189 |
| 2014/0278253 A1 | 9/2014 | Beymore | |
| 2014/0278254 A1 | 9/2014 | Beymore | |
| 2015/0023054 A1 | 1/2015 | Goda et al. | |
| 2015/0127269 A1 * | 5/2015 | Bell | G01N 33/32 |
| | | | 702/22 |
| 2015/0134269 A1 | 5/2015 | Norris | |
| 2015/0134299 A1 | 5/2015 | Norris | |
| 2015/0134300 A1 | 5/2015 | Norris | |

FOREIGN PATENT DOCUMENTS

| | | | | |
|---|---|---|---|---|
| CN | 1797420 | | 7/2006 | |
| CN | 101184986 | | 5/2008 | |
| CN | 101646929 | | 2/2010 | |
| CN | 101784871 | | 7/2010 | |
| CN | 102549545 | | 7/2012 | |
| JP | 07150081 | | 6/1995 | |
| JP | H 10-324829 A | | 12/1998 | |
| JP | H 11-230831 A | | 8/1999 | |
| JP | 2001088393 | * | 4/2001 | B41J 21/00 |
| JP | 2001-338091 A | | 12/2001 | |
| JP | 02001338091 | * | 12/2001 | G06F 17/60 |
| JP | 2002236850 | | 8/2002 | |
| JP | 2003-294622 A | | 10/2003 | |
| JP | 2005-528603 A | | 9/2005 | |
| JP | 2006277555 | | 10/2006 | |
| JP | 2007218895 | | 8/2007 | |
| JP | 2010242018 | | 10/2010 | |
| KR | 20100102147 | | 9/2010 | |
| TW | 200608310 | | 3/2006 | |
| TW | 200821602 | | 5/2008 | |
| TW | 200834273 | | 8/2008 | |
| TW | 201339652 A | | 10/2013 | |
| WO | 03/063719 A2 | | 7/2003 | |
| WO | 2006096521 | | 9/2006 | |
| WO | 2006112864 | | 10/2006 | |
| WO | 2007096402 | | 1/2009 | |
| WO | 2013049792 A1 | | 4/2013 | |
| WO | 2013116192 | | 8/2013 | |
| WO | 2014150337 | | 9/2014 | |

OTHER PUBLICATIONS

JP 2010242018, 11 pages (Year: 2010).*
Espacenet English abstract of CN 1635957 A.
Espacenet English abstract of TW 201339652 A.
Anonymous, "Chapter 1.3.5.17. Detection of Outliers", NIST/SEMATECH e-Handbook of Statistical Methods, Jan. 1, 2012, XP055162021.
Paravina et al, "Evaluation of blending effect of composites related to restoration size", Dental Materials, Elsevier, Amsterdam, NL, vol. 22, No. 4, Apr. 1, 2006, pp. 299-307, XP027943381, ISSN: 0109-5641 table 2.
Takagi et al, "Prediction of spectral reflectance factor distribution of color-shift paint finishes", Color Research & Application, John Wiley & Sons, Inc., US, vol. 32, No. 5, Oct. 1, 2007, pp. 378-387, XP002604927, ISSN: 0361-2317.
Beymore, Paul M., U.S. Appl. No. 14/121,869, "Pigment Identification of Complex Coating Mixtures with Sparkle Color", filed Oct. 28, 2014.
Non-Final Office Action for U.S. Appl. No. 14/535,399 dated Apr. 4, 2017.
Final Office Action for U.S. Appl. No. 14/535,399 dated Nov. 1, 2017.
Non-Final Office Action in U.S. Appl. No. 14/535,380 dated Apr. 12, 2017.
Office Action in application No. 201480070100.X dated Feb. 27, 2017.
Final Office Action for U.S. Appl. No. 14/535,380 dated Oct. 27, 2017.
Non-Final Office Action for U.S. Appl. No. 13/832,116 dated Mar. 5, 2014.
"Kuncheva, Ludmila I., James C. Bezdek, and Robert PW Duin. ""Decision templates for multiple classifier fusion: an experimental comparison"" Patternrecognition 34.2. 2001."
Korean Office Action in application No. 201507025129 dated Jun. 21, 2016.
Final Office Action for application No. 13832554 dated Apr. 20, 2016.
I. Lissner, U. Philipp: "Upgrading Color-Difference Formulas", Journal of the Optical Society of America, vol. 27 No. 7, Jun. 11, 2010 (Jun. 11, 2010), pp. 1620-1629, XP055152562, DOI: 10,1364/JOSAA.27.001620 Sections 1 and 2.A.

(56) References Cited

OTHER PUBLICATIONS

D. Puig, M.A. Garcia, J. Melendez: "Application-Independent feature selection for texture classification", Pattern Recognition, vol. 43, No. 10, May 10, 2010 (May 10, 2010) pp. 3182-3297, XP027095420, DOI: 10. 1016/j.patcog.2010.05.005 abstract and section 3.
J.H. Xin, S. Shao, K.F.-L. Chung: "Colour-appearance modelling using feedforward networks with Bayesian regularization method—part 1: forward model", Color Research & Application, vol. 25, No. 6, Oct. 13, 2000, pp. 424-434, XP055152560, DOI: 10.1002/1520-6378(200012)25:6<424:AID-COL7>3.0.CO;2-Q.
E. Kirchner: "Appearance and measurement modeling an drendering of the visual texture of automotive paints", Detroit Color Council, Mar. 13, 2013, XP055153196, Retreived from the Internet: URL: http://www.detroitcc.org/files/2013March14b.pdf, [retireved on Apr. 3, 2013] Models for predicting Texture.
E.J.J. Kirchner, J. Ravi: "Setting tolerances on color and texture for automotive coatings", Color Research & Application, vol. 39, No. 1, Jul. 25, 2012 pp. 88-98, XP055152561, DOI:10.1002/col.21767.
PPG Automotive Refinish: "RapidMatch™ X-5:guida utente", Pittsburgh Plate Glass (PPG) Industries, 2013, XP055153237, retireved from the Internet: URL:http://it.nexaautocolor.com/media/213903/rapidmatch_v1-2012_email_version.pdf [retrieved on Sep. 22, 2014].
Non-Final Office Action for U.S. Appl. No. 13/832,554 dated Sep. 23, 2015.
Kokla, Vassiliki et al., A Bayesian decision model for watercolour analysis, Proc. of SPIE, 2007, vol. 6618, pp. 66180S-1-66180S-9.
Korean Office Action for application No. 2015/7025129 dated Dec. 29, 2016.
Chinese Office Action for application No. 201480015524.6 dated Dec. 26, 2016.
Final Office Action for U.S. Appl. No. 13/832,554 dated Sep. 6, 2017.
Non-Final Office Action for U.S. Appl. No. 13/832,554 dated May 2, 2017.
*Alice* vs *CLS Bank* (Supreme Court Decision) (2013).
Notice of Allowance from U.S. Appl. No. 13/835,675 dated Nov. 1, 2016.
Non-Final Office Action from U.S. Appl. No. 13/835,675 dated Sep. 16, 2015.
Taiwan Office Action for application No. 103109480 dated Sep. 17, 2015.
Taiwan Office Action for application No. 103109480 completed on Jul. 17, 2016.
Korean Office Action in application No. 2015-7025121 dated Jul. 25, 2016.
International Search Report for application No. PCT/US2014/022983 dated Nov. 28, 2014.
Korean Office Action in application No. 2015-7025121 dated Jan. 31, 2017.
Chinese Office Action in application No. 201480015523.1 dated Feb. 7, 2017.
Non-Final Office Action in U.S. Appl. No. 13/835,675 dated May 2, 2017.
Final Office Action for U.S. Appl. No. 13/835,675 dated Dec. 12, 2017.
Non-Final Office Action for U.S. Appl. No. 13/832,554 dated Dec. 12, 2017.
Wang Qiang, "Texture Analysis and Classification Based on Bayesian Network Model", Computer Aided Design & Computer Graphics, Dec. 31, 2007, pp. 1565-1568.
Takuro Yonezawa, "An Event Decription Language Using Temporal Relation for Smart Object Services", IPSJ SIG Technical Report 2008-MBL-44, Mobile computing and ubiquitous communication, 2008-UBI-17, Ubiquitous computing system, Information Processing Society of Japan, Feb. 27, 2008, vol. 2008, No. 18, pp. 75-82.
Japanese Office Action for application No. JP 2016-501119 dated Nov. 7, 2016.
Final Office Action for U.S. Appl. No. 13/832,554 dated Mar. 26, 2018.
Massonnet et al., "Identification of organiz pigments in coatings: applications to red automotive topcoats", First Neeting of the European Academy of Forensic Sciences, 1997.
Harkins et al., Identification of pigments in paint products by infrared spectroscopy, Analystical Chemistry, 1959.
Janina et al., "Examination of multilayer paint coats by the use of infrared, Raman and XRF spectroscopy for forensic purposes", J. of Molecular Structure, 2006.
Rafik, "Bulk optical properties of phthalocyanine pigment particles", Can J. Chem, 1980.
Non-Final Office Action for U.S. Appl. No. 14/535,380 dated Apr. 2, 2018.
Office Action dated May 29, 2018 from Korean Patent Application No. 2016-7015257 filed Nov. 10, 2014.
Office Action dated Nov. 16, 2017 from Korean Patent Application No. 2016-7015257 filed Nov. 10, 2014.
Decision to Grant dated Jul. 12, 2018 from Korean Patent Application No. 2016-7015257 filed Nov. 10, 2014.
International Search Report dated Feb. 19, 2015 from International Patent Application No. PCT/US2014/064786 filed Nov. 10, 2014.
International Preliminary Report on Patentability dated May 10, 2016 from International Patent Application No. PCT/US2014/064786 filed Nov. 10, 2014.
Office Action dated May 27, 2017 from Chinese Patent Application No. 201480070098.
Office Action dated Feb. 11, 2018 from Chinese Patent Application No. 201480070098 filed Nov. 10, 2014.
Notification to Grant Patent Right dated Jul. 4, 2018 from Chinese Patent Application No. 201480070098 filed Nov. 10, 2014.
Search Report dated May 17, 2017 from Chinese Patent Application No. 201480070098 filed Nov. 10, 2014.
Office Action dated May 23, 2017 from Japanese Patent Application No. 2016528177 filed Nov. 10, 2014.
Office Action dated Dec. 19, 2017 from Japanese Patent Application No. 2016528177 filed Nov. 10, 2014.
Decision to Grant dated Jul. 25, 2018 from Japanese Patent Application No. 2016528177 filed Nov. 10, 2014.
Office Action dated Mar. 27, 2017 from Canadian Patent Application No. 2930021 filed Nov. 10, 2014.
Office Action dated Mar. 12, 2018 from Canadian Patent Application No. 2930021 filed Nov. 10, 2014.
Office Action dated Dec. 21, 2018 from Canadian Patent Application No. 2930021 filed Nov. 10, 2014.
Office Action dated Sep. 16, 2016 from Australian Patent Application No. 2014346526 filed Nov. 10, 2014.
Office Action dated Jan. 25, 2017 from Australian Patent Application No. 2014346526 filed Nov. 10, 2014.
Office Action dated Jun. 29, 2017 from Australian Patent Application No. 2014346526 filed Nov. 10, 2014.
Acceptance Notice dated Sep. 20, 2017 from Australian Patent Application No. 2014346526 filed Nov. 10, 2014.
Office Action dated Jan. 2, 2019 from Indian Patent Application No. 201617016018 filed May 7, 2016.
Office Action dated Oct. 9, 2018 from U.S. Appl. No. 14/535,399, filed Nov. 7, 2014.
Office Action dated Feb. 5, 2019 from U.S. Appl. No. 14/535,399, filed Nov. 7, 2014.
Notice of Allowance dated Apr. 18, 2019 from U.S. Appl. No. 14/535,399, filed Nov. 7, 2014.

* cited by examiner

TEXTURE ANALYSIS OF A COATED SURFACE USING ELECTROSTATICS CALCULATIONS

CROSS REFERENCE TO RELATED APPLICATION

The present application claims priority to U.S. Provisional Application No. 61/901,493, filed on Nov. 8, 2013.

FIELD OF THE INVENTION

Embodiments of the present invention generally relate to the use of electrostatics methods to relate spectral reflectances or colorimetric information from spectrophotometric angles and/or incident light sources to identify the proper pigment(s) to match both the texture and/or gonioapparent effect(s) occurring within an unknown target coating.

BACKGROUND OF THE INVENTION

In a standard portable spectrophotometer, the incident light is generally set at an angle of forty-five (45) degrees from normal. The resulting spectral reflectances that can be gathered are generally in the same plane as the incident light and are on either side of the specular angle (equal and opposite angle to the incident light) as well as nearer to the incident light source itself.

New portable spectrophotometric devices offer a vast multitude of angular color response (spectral reflectance) data. Besides the addition of several new angles, including azimuthal, or out-of-plane, angles, many instruments also offer additional light sources with different geometries from standard. By way of example, the incident light source of a second illuminator may be located at fifteen (15) degrees from normal. The plurality of combinations of incident light and angular response can be both too little and too much information to be handled at one time.

Thus, there is a need for systems and methods that may be used to evaluate all of the data and specific combinations of data from a spectrophotometer.

SUMMARY OF THE INVENTION

In a first aspect, embodiments of the invention provide a computer implemented method. The method includes obtaining, using a processor, reflectance data from a target coating and calculating, using the processor, electrostatics data from the reflectance data. The method also includes generating, using the processor, a coating formulation that is the same or substantially similar in appearance to the target coating.

In another aspect, embodiments of the invention are directed to a system. The system includes a database or processor in communication with the database. The processor is programmed to obtain reflectance data from a target coating, calculate electrostatics data, and generate a coating formulation that is the same or substantially similar in appearance to the target coating.

In another aspect, embodiments of the invention provide an apparatus. The apparatus includes means for obtaining reflectance data from a target coating and means for calculating electrostatics data. The apparatus also includes means for generating a coating formulation that is the same or substantially similar in appearance to the target coating.

In a further aspect, embodiments of the invention provide a non-transitory computer readable medium including software for causing a processor to: obtain reflectance data from a target coating; calculate electrostatics data; and generate a coating formulation that is the same or substantially similar in appearance to the target coating.

DETAILED DESCRIPTION OF THE INVENTION

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Embodiments of the invention are directed generally to spectral analysis of coatings, and more particularly, but not by way of limitation, to devices, methods and systems for predicting and formulating a complex coating mixture containing metallic, pearlescent, and/or special effect pigments.

In various embodiments, the present invention generally relates to a method and apparatus for identifying physical property attributes of cured complex coating (e.g., paint) mixtures using electrostatics data that are calculated, using a processor, based on the spectral reflectance and colorimetric response from a spectrophotometer.

In various embodiments, the purpose of using an electrostatics methodology is multi-fold. First, in order to use all available angles within a given system, electrostatics may be used to create an alternate bi-directional reflectance distribution function ("BRDF")-type analysis. This type of analysis does not exclude any angles, but uses all angles to create a hemispherical "map" or "fingerprint" of a particular texture or pigment type, whether gonioapparent or not. Second, electrostatics may be used to evaluate only specific combinations of angles in order to achieve purposeful manipulations. Similarly, this includes the specific exclusion of specific singular angles or combinations of angles when a particular texture or effect is being sought after as included or not included in a target coating. Third, electrostatics may be used to accommodate for and correct the potential assumption that the received spectral reflectance values are incorrect in some way. Some potential reasons for irregularity or abnormality of the spectral reflectance data, even if minor, may include incident light angle location, incident light fluctuation, aperture size, target coating surface non-uniformity, etc.

Figure 1:
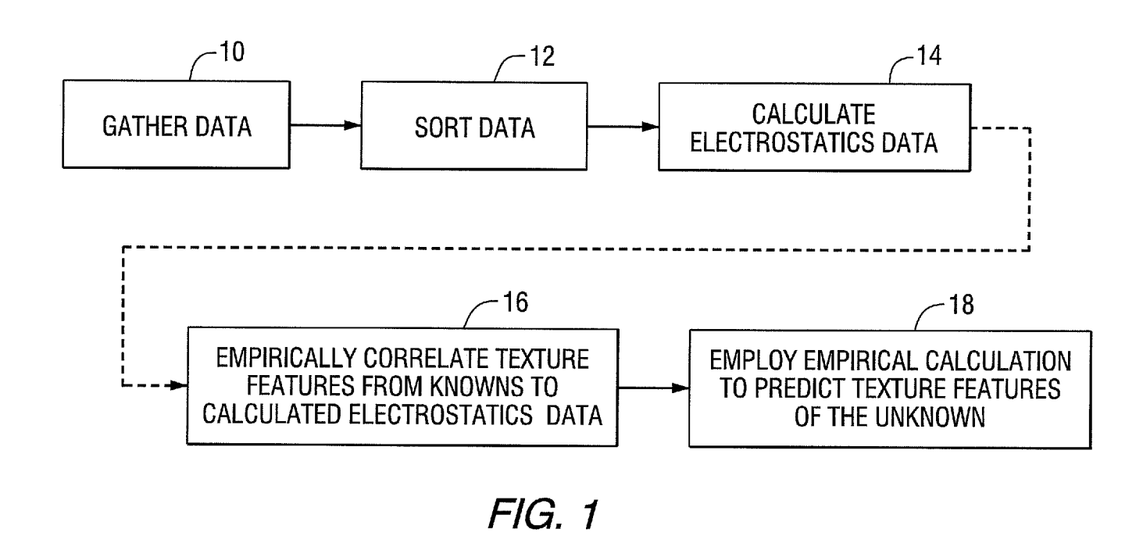
FIG. 1 illustrates an embodiment of a process that calculates a formula for a target complex coating.
Figure 2:
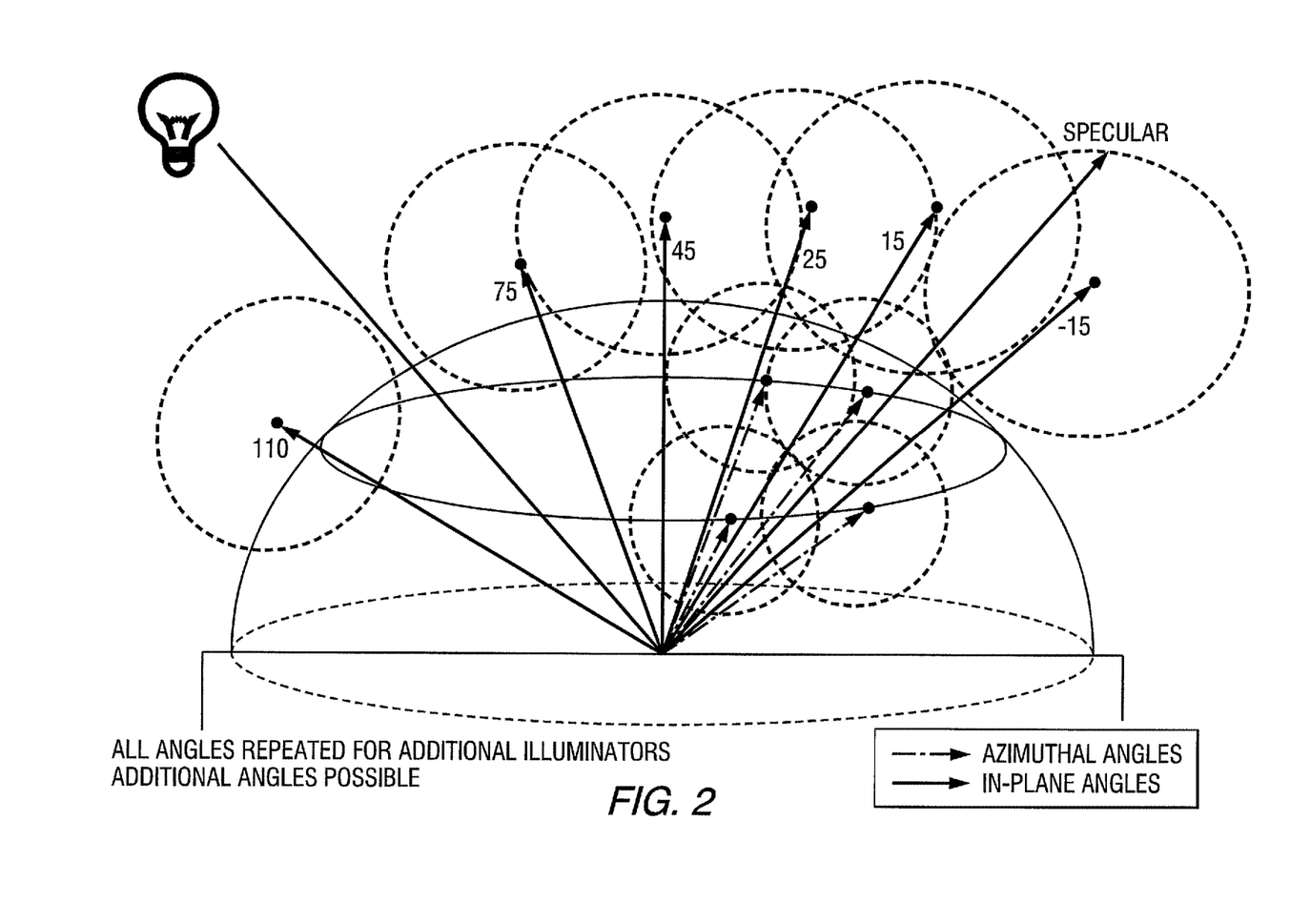
FIGS. 2 and 3 illustrate a pseudo-electric field.
Figure 3:
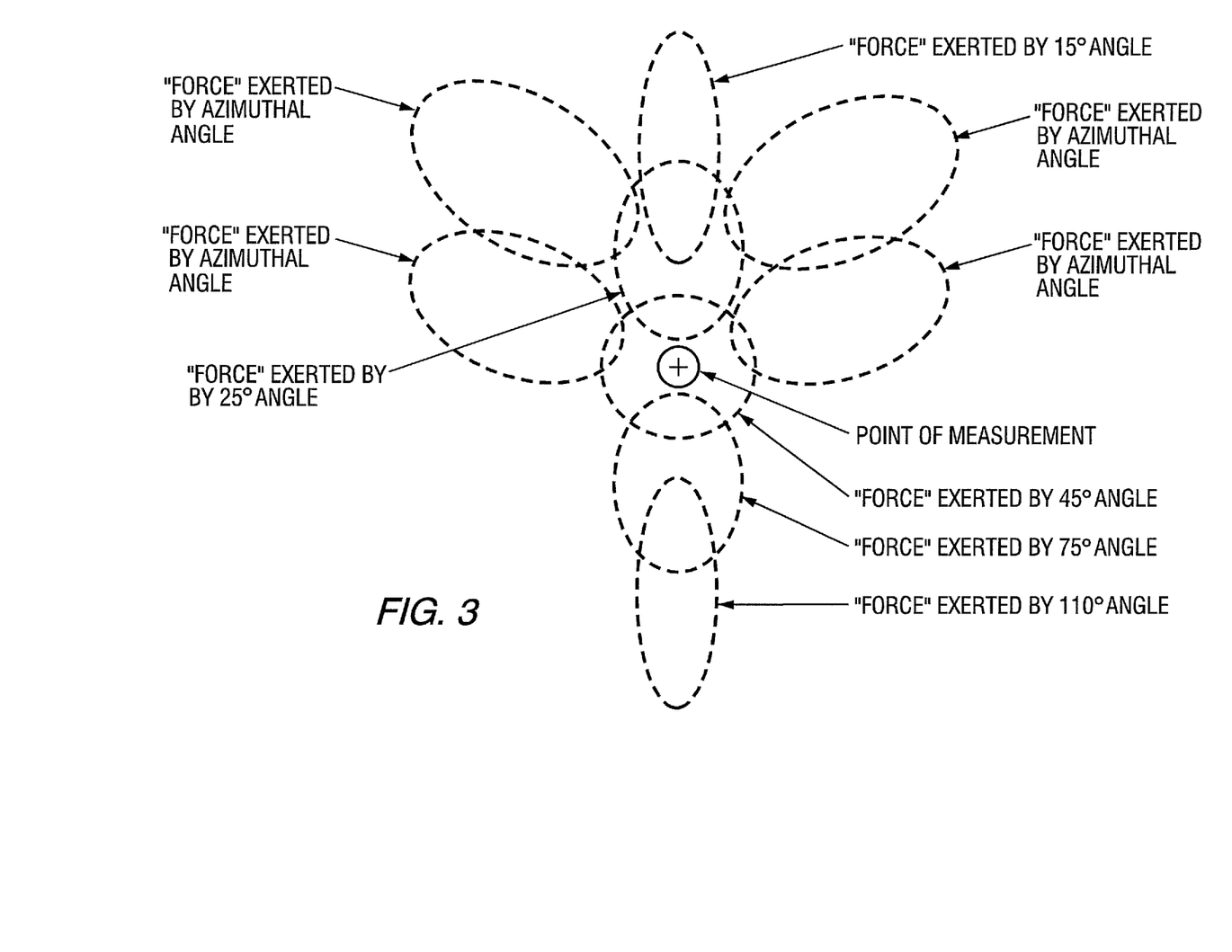

FIG. 1 illustrates an embodiment of a process that calculates a formula for a target complex coating. At step 10, data is gathered from, for example, a spectrophotometer and, at step 12, the data are sorted based on a secondary array of associated information. At step 14, electrostics data is calculated. In various embodiments, the way that individual reflectances colorimetric information at specific physical angular ports, or angles in conjunction with the incident light angle, will act as point charges in an effect of influencing electrostatic "forces" on other reflectances across the physical layout of, for example, a portable spectrophotometer may be shown. A pseudo-electric field may be created as illustrated in FIGS. 2 ("standard" view) and 3 ("top down" view). Based on the number of point charges (reflectances or colorimetric information) that are desired for comparison at a single time, Coulomb's Law may be used to define the electric field or force between point charges created by a single point charge or between multiple point charges. In a simplistic form, Coulomb's Law is as follows for two point charges:

$$F = \frac{Q_1 Q_2}{4\pi r^2 \varepsilon_0} \quad \text{Equation (1)}$$

where $Q_1$ and $Q_2$ are the point electric charges, or in the case of texture analysis, the reflectance at a particular angle and wavelength or colorimetric information at that angle, r is the distance between the two point charges on the surface of the sphere, and $\varepsilon_0 = 8.854187817 \times 10^{-12}$. In various embodiments, if reflectance values are used as the point charge values, they are wavelength dependent. Therefore, in various embodiments the calculation occurs individually for each wavelength and is integrated at the end-usage point of the data.

In various embodiments, in order to calculate the distance, r, between the two point charges, one possible solution is to use a portion of a great circle distance calculation which may be used by employing a special form of the Vincenty formula to calculate the spherical angle between the two point charges:

$$\Delta \hat{\sigma} = \arctan\left( \frac{\sqrt{(\cos\phi_f \sin\Delta\lambda)^2 + (\cos\phi_s \sin\phi_f - \sin\phi_s \cos\phi_f \Delta\lambda)^2}}{\sin\phi_s \sin\phi_f + \cos\phi_s \cos\phi_f \cos\Delta\lambda} \right) \quad \text{Equation (2)}$$

where $\Phi_f$, $\lambda_f$, and $\Phi_s$, $\lambda_s$ are coordinate locations, in radians, of the point charges on the surface of a sphere. The distance, r, then follows as:

$$r = R \Delta\sigma \quad \text{Equation (3)}$$

where R is the radius of the sphere. In the case of a portable spectrophotometer, in various embodiments this may be assumed to equal 1 or may be accurately measured. In various embodiments, the value for R does not change because it is likely the same or a similar spectrophotometer model will be used, and thus R remains constant. If it is expected that R may, in fact change then R may be appropriately measured and accounted for in Equation 3.

In various embodiments, in order to use the special form of the Vincenty formula, spatial coordinates, or latitude and longitude, for the point charges (reflectances or colorimetric data) may be assigned. The spatial coordinate assignments may be created using the physical angular layout of the spectrophotometer. By way of example, in various embodiments the spatial coordinates of the point charges may become coordinates that are functions of at least one of (1) a version of the angle reflected light, which may be dependent upon the incident light angle; (2) an indication of in-plane or out-of-plane as well as location within that plane; (3) spectral reflectance value or colorimetric value at a particular wavelength. While a two point charge example is shown for the particular form of Coulomb's Law, in various embodiments any single or multiple combinations of angular point charges may be used with various forms of Coulomb's Law. Additionally, other electrostatics calculations, such as electric field, electric potential, etc. may be used in place of or in conjunction with Coulomb's Law force equation. The potential for singular, paired, triplicate, etc. comparisons may provide a sizeable amount of information, which may be used to identify texture. In various embodiments the incident light angle, either from normal or from parallel, may be used within the coordinate definitions of other angular data. This may be useful when working with data from multiple incident light angles or when including a comparison of the data received from the same physical receptor on the instrument, however the incident light came from multiple angles.

In various embodiments, when using spectral reflectance data, the calculation may occur individually for each wavelength. Statistics, such as for example mean, median, and sum may be used to create a singular value out of multiple wavelength calculated electrostatics values. In another embodiment, an individual specific wavelength or wavelengths may be compared between electrostatics analysis. The value of such a situation is to focus on the wavelength or wavelengths of maximum reflectance, and potentially secondary maximum reflectance, where a majority of color and/or texture information is visibly perceived within the visible spectrum. An analysis of shifting maximum reflectances by wavelength may also be completed using electrostatics analysis.

At step 16 of FIG. 1, the calculated electrostatics values from the colorimetric or spectral reflectance data may further be empirically correlated to known characteristics in order to identify textures, primary flake types, or other appearance information in complex coating mixtures. To employ an empirical method, the electrostatics data points (force, field, potential, etc.) are calculated for an empirical dataset and all desired combinations of angles, representative of the expected mixtures and colors that will need to be handled in everyday situations. The empirical data set may be used to create a predictive correlation: $y = f(x)$, where y represents the desired characteristic for identification or a qualitative question regarding the target coating, and $f(x)$ is some function of x's, where x is one or multiple variables using the electrostatics calculated values from a specific set or multiple sets of angular considerations. In various embodiments it may be desirable to limit the angular comparison sets to the specific sets that are most feature-defining for the particular characteristic that is being identified. The resulting function may be linear or non-linear as defined by the empirical data set.

Figure 4:
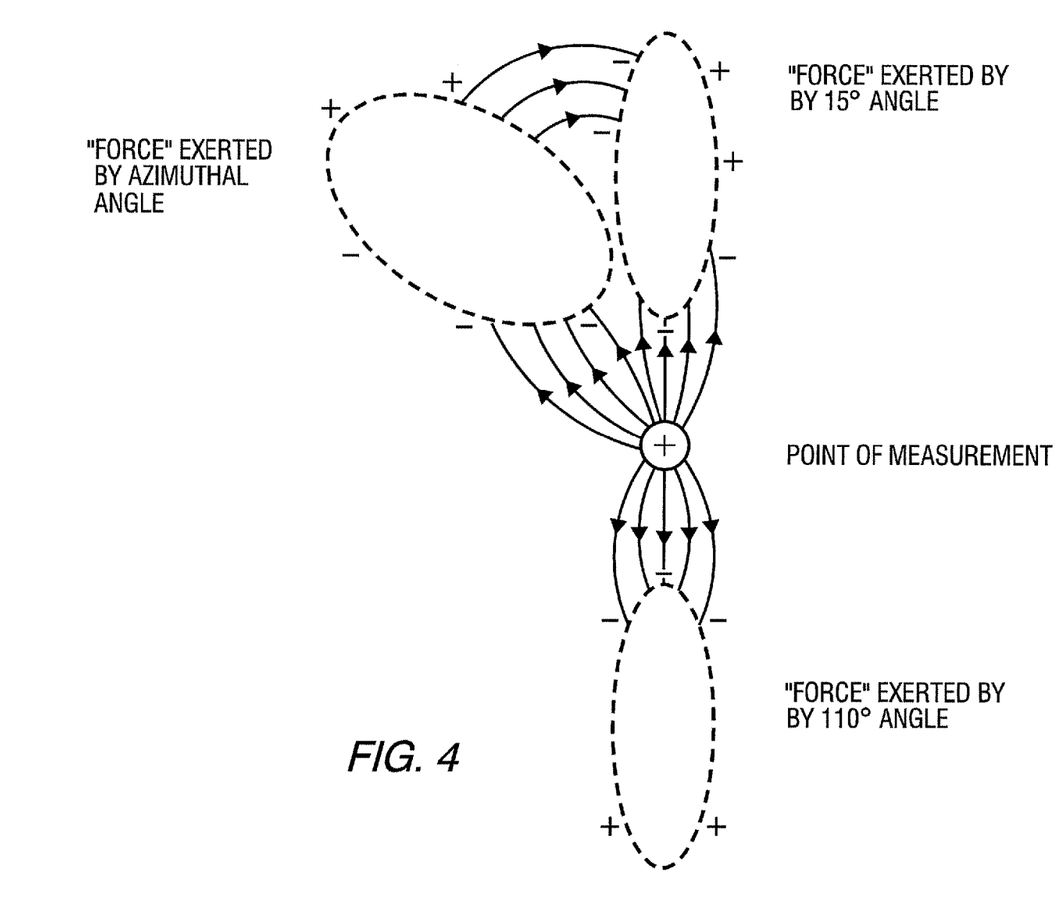
FIG. 4 illustrates an example of the use of an electrostatic field using a specific combination of angles to predict whether or not a target coating will contain a gonioapparent effect.

FIG. 4 illustrates an example of the use of an electrostatic field using a specific combination of angles to predict whether or not a target coating will contain a gonioapparent effect.

Figure 5:
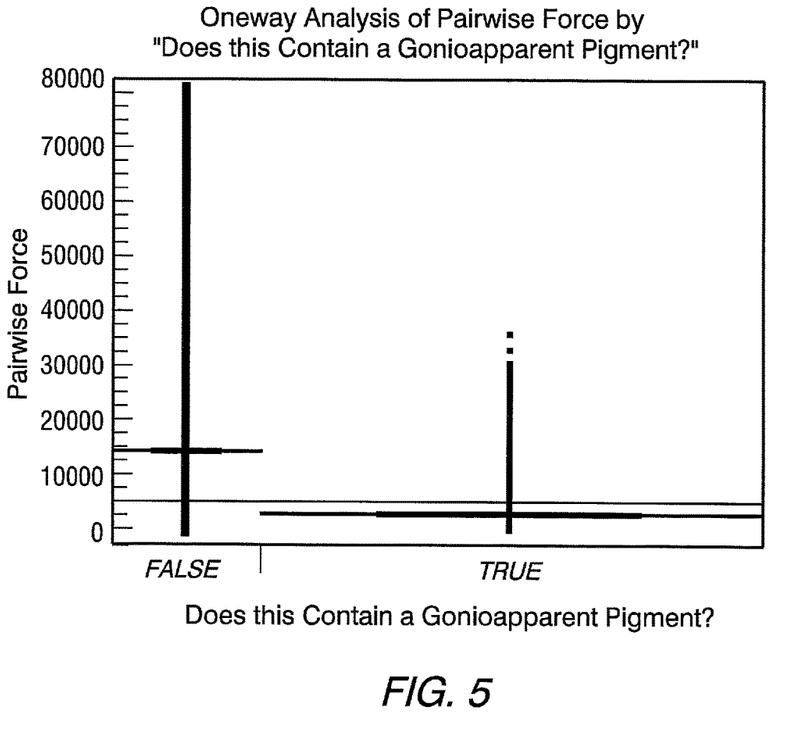
FIG. 5 illustrates an example of an empirical correlation of two different angle electrostatics data compared in a pairwise manner versus whether the target coating contains a specific gonioapparent pigment.

FIG. 5 illustrates an example of an empirical correlation of two different angle electrostatics data compared in a pairwise manner versus whether the target coating contains a specific gonioapparent pigment. In this example, a calculated electrostatics value of the same pairwise angular combination resulting in a value over roughly 5500 indicates a greater likelihood of containing gonioapparent pigment versus not containing a gonioapparent pigment.

Figure 6:
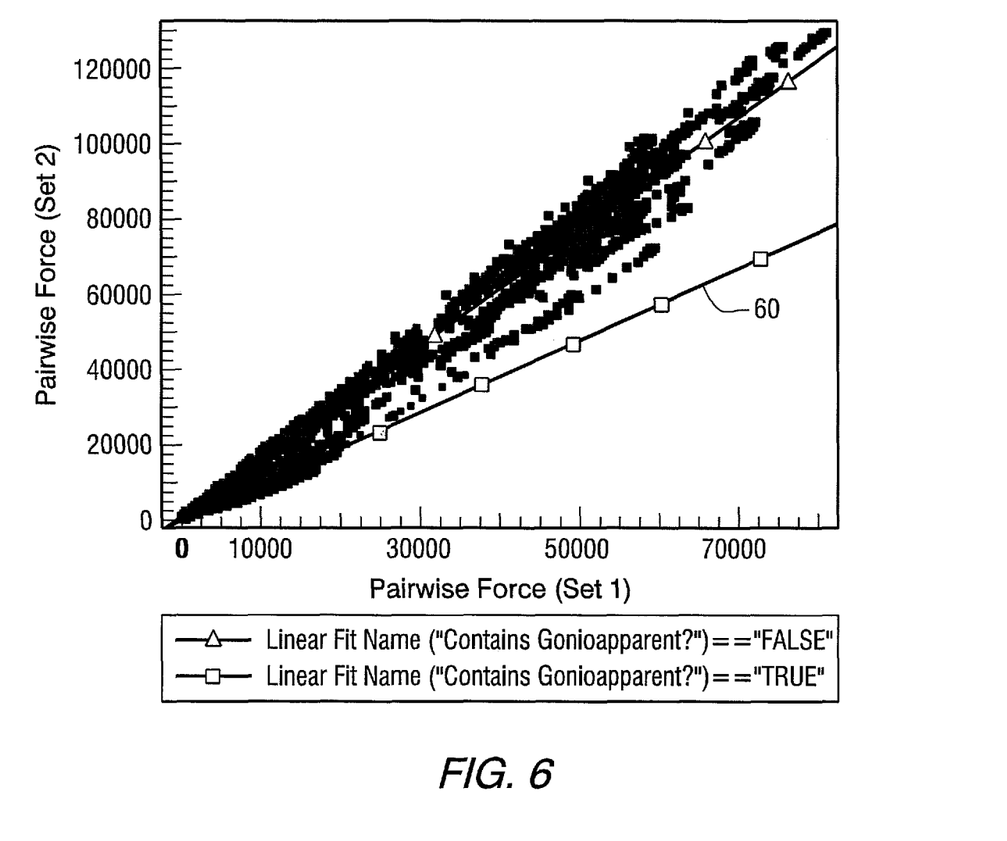
FIG. 6 illustrates a different type of example of another form of an empirical correlation.

FIG. 6 illustrates a different type of example of another form of an empirical correlation. In this example scenario, two sets of pairwise angular comparisons using electrostatics calculated data are graphed versus one another. To use the correlation, the target coating's values may be input in the electrostatics calculations and whichever linear correlation's resultant graphical value it is more closely aligned to offers a higher likelihood of that effect being present. In many cases, the degree of likelihood may also be assessed based on a residual calculation from the correlations that were originally empirically determined. In such an example, a target coating calculated electrostatics value closer to correlation line 60 ("TRUE") indicates a higher likelihood of the target coating containing the specific gonioapparent effect versus not containing that effect.

Once an empirical correlation has been determined, at step 18 of FIG. 1 it may be used to derive the predicted value for the target coating. This may be achieved by using the target coating's values for the x's (electrostatic force, field, potential, etc.) and calculating the answer for y (the texture effect). While examples have been given herein for the content of a gonioapparent pigment, embodiments of the present invention may derive a result as specific as which gonioapparent pigment at which size flake of that pigment by iteratively choosing the most important single angles or combinations of angles for the electrostatics calculations and empirical correlations. The choice of angular comparisons and to what level they are combined may be used to create the best possible empirical correlation. In various embodiments, empirical correlations may also be improved by including other non-electrostatics information, for example singular angle colorimetric data.

In various embodiments, the quality of the overall "map," or "fingerprint," approach and the quality of the empirical correlation approach may be dependent upon the quality of the input data. The quality of the input data may be dependent upon the quality of the instrumentation and the quality of the data set used to create a set of known for the overall map or the empirical correlation. While any quality of data from an instrument or an empirical data set will result in an answer, the answer may be improved with the use of a high quality instrument and a widely varied, high quality empirical data set.

The entire set of calculations described herein may be used in conjunction with a processor in order to facilitate the choice of specific angle combination as well as accommodate the volume of calculations required in order to derive and then use an empirical correlation using electrostatics data.

Figure 7:
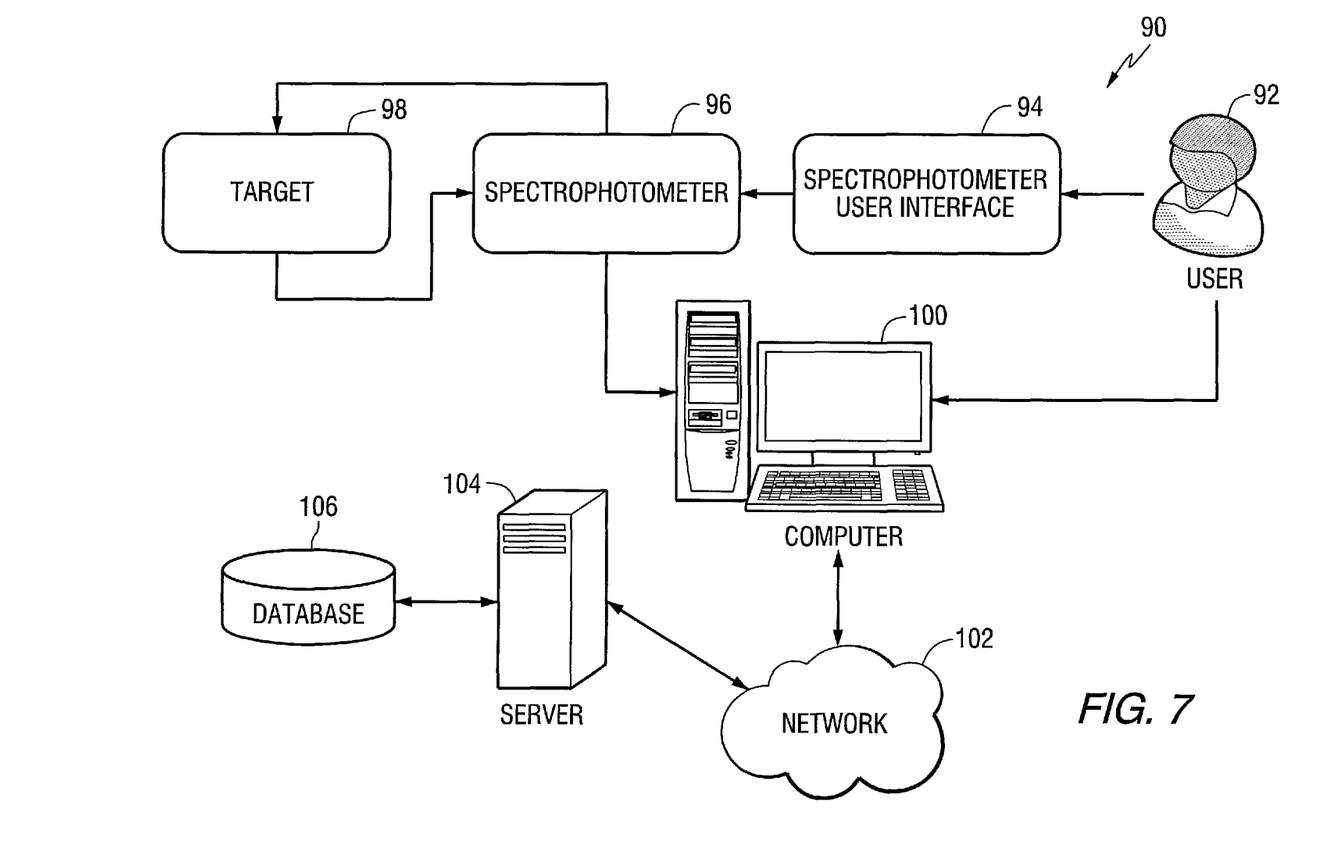
FIG. 7 illustrates an embodiment of a system which may be used to identify physical property attributes of a coating mixture of a target sample.

FIG. 7 illustrates an embodiment of a system 90 which may be used to identify physical property attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used by the methods of embodiments of the present invention for comparison purposes. In various embodiments the database 106 may be utilized in, for example, a client server environment or in, for example, a web based environment such as a cloud computing environment. Various steps of the methods of embodiments of the present invention may be performed by the computer 100 and/or the server 106.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Accordingly, the particular embodiments described in detail herein are illustrative only and are not limiting to the scope of the invention.

What is claimed is:

1. A computer implemented method, comprising:
obtaining, from a spectrophotometric device, reflectance data from a target coating;
generating, using the processor, a hemispherical map based upon electrostatics data calculated from the reflectance data by solving Coulomb's Law with at least a portion of the reflectance data being mathematically treated as a point electric charge, wherein the hemispherical map corrects for irregularities and abnormalities in the spectral reflectance data;
comparing the hemispherical map to corresponding hemispherical maps stored within an empirical dataset, wherein the corresponding hemispherical maps are each associated with one or more pigments and textures; and
generating based upon the comparison of the hemispherical maps, using the processor, a coating formulation that is the same in appearance to the target coating;
whereby generating a hemispherical map, based upon electrostatics data calculated by solving Coulomb's Law, utilizes all available angles within a given spectrophotometric device.

2. The method of claim 1, wherein generating a coating formulation comprises correlating the electrostatics data to a plurality of known data and predicting at least one texture feature of the target coating based on the correlating.

3. The method of claim 2, wherein correlating the electrostatics data to a plurality of known data comprises empirically correlating the electrostatics data to a plurality of known data.

4. The method of claim 2, wherein predicting at least one texture feature of the target coating based on the correlating comprises predicting, using at least one empirical calculation, at least one texture feature of the target coating based on the correlating.

5. A system, comprising:
a database; and
a processor in communication with the database and programmed to:
obtain, from a spectrophotometric device, reflectance data from a target coating;
generate a hemispherical map based upon electrostatics data calculated by solving Coulomb's Law with at least a portion of the reflectance data being mathematically treated as a point electric charge, wherein the hemispherical map corrects for irregularities and abnormalities in the spectral reflectance data;
compare the hemispherical map to corresponding hemispherical maps stored within an empirical dataset, wherein the corresponding hemispherical maps are each associated with one or more pigments and textures; and
generate based upon the comparison of the hemispherical maps a coating formulation that is the same in appearance to the target coating;
whereby generating a hemispherical map, based upon electrostatics data calculated by solving Coulomb's Law, utilizes multiple angles within a given spectrophotometric device.

6. The system of claim 5, further comprising calculating a distance between two point charges within Coulomb's Law by solving a Vincenty formula.

7. An apparatus, comprising:
means for obtaining reflectance data from a target coating;
means for generating a hemispherical map based upon electrostatics data calculated by solving Coulomb's Law with at least a portion of the reflectance data being mathematically treated as a point electric charge, wherein the hemispherical map corrects for irregularities and abnormalities in the spectral reflectance data;
means for comparing the hemispherical map to hemispherical maps stored within an empirical dataset, wherein the corresponding hemispherical maps are each associated with one or more pigments and textures; and
means for generating based upon the comparison of the hemispherical maps a coating formulation that is the same in appearance to the target coating;
whereby generating a hemispherical map, based upon electrostatics data calculated by solving Coulomb's Law, utilizes multiple angles within a given spectrophotometric device.

8. The apparatus of claim 7, wherein the means for generating a coating formulation comprises means for correlating the electrostatics data to a plurality of known data and means for predicting at least one texture feature of the target coating based on the correlating.

9. The apparatus of claim 8, wherein the means for correlating the electrostatics data to a plurality of known data comprises means for empirically correlating the electrostatics data to a plurality of known data.

10. The apparatus of claim 8, wherein the means for predicting at least one texture feature of the target coating based on the correlating comprises means for predicting, using at least one empirical calculation, at least one texture feature of the target coating based on the correlating.

11. A non-transitory computer readable medium including software for causing a processor to:
obtain reflectance data from a target coating;
generate a hemispherical map based upon electrostatics data calculated by solving Coulomb's Law with at least a portion of the reflectance data being mathematically treated as a point electric charge, wherein the hemispherical map corrects for irregularities and abnormalities in the spectral reflectance data;
compare the hemispherical map to corresponding hemispherical maps stored within an empirical dataset, wherein the hemispherical maps are each associated with one or more pigments and textures; and
generate, based upon the comparison of the hemispherical maps, a coating formulation that is the same in appearance to the target coating;
whereby generating a hemispherical map, based upon electrostatics data calculated by solving Coulomb's Law utilizes, multiple angles within a given spectrophotometric device.

* * * * *